(12) United States Patent
Matsuura et al.

(10) Patent No.: US 10,364,216 B2
(45) Date of Patent: Jul. 30, 2019

(54) ALKENYL SULFATE ESTER OR SALT THEREOF

(71) Applicant: Kao Corporation, Chuo-ku, Tokyo (JP)

(72) Inventors: Masanori Matsuura, Kawasaki (JP); Tomohiro Nakagawa, Funabashi (JP); Keiichi Yoshikawa, Saitama (JP)

(73) Assignee: Kao Corporation, Tokyo (JP)

( * ) Notice: Subject to any disclaimer, the term of this patent is extended or adjusted under 35 U.S.C. 154(b) by 501 days.

(21) Appl. No.: 14/917,178

(22) PCT Filed: Aug. 1, 2014

(86) PCT No.: PCT/JP2014/070380
§ 371 (c)(1),
(2) Date: Mar. 7, 2016

(87) PCT Pub. No.: WO2015/040967
PCT Pub. Date: Mar. 26, 2015

(65) Prior Publication Data
US 2016/0198746 A1 Jul. 14, 2016

(30) Foreign Application Priority Data

Sep. 19, 2013 (JP) .................. 2013-194188
Jul. 31, 2014 (JP) .................. 2014-156598
Jul. 31, 2014 (JP) .................. 2014-156599

(51) Int. Cl.
*C07C 305/14* (2006.01)
*A23L 27/30* (2016.01)
*A23L 27/00* (2016.01)

(52) U.S. Cl.
CPC .......... *C07C 305/14* (2013.01); *A23L 27/39* (2016.08); *A23L 27/88* (2016.08); *A23V 2002/00* (2013.01)

(58) Field of Classification Search
CPC ......... C07C 305/14; A23L 27/88; A23L 27/39
USPC ......................................... 426/548
See application file for complete search history.

(56) References Cited

U.S. PATENT DOCUMENTS

2006/0257543 A1* 11/2006 Tachdjian .............. A23L 27/20
                                                                426/534
2006/0286259 A1* 12/2006 Hargreaves .............. A23L 2/02
                                                                426/590

FOREIGN PATENT DOCUMENTS

| JP | 08-034767 A | 2/1996 |
| JP | 09-169720 A | 6/1997 |
| JP | 2001-294545 A | 10/2001 |
| JP | 2007-209268 A | 8/2007 |
| JP | 2009-051909 A | 3/2009 |
| JP | 2013-017459 A | 1/2013 |
| JP | 5314207 B | 10/2013 |
| JP | 2014-176322 A | 9/2014 |
| JP | 5674984 B | 2/2015 |
| JP | 2015-082998 A | 4/2015 |

OTHER PUBLICATIONS

International Search Report (ISR) for PCT/JP2014/070380; I.A. fd Aug. 1, 2014, dated Oct. 7, 2014, from the Japanese Patent Office, Tokyo, Japan.

International Preliminary Report on Patentability (IPRP), Chapter I of the Patent Cooperation Treaty, including the Written Opinion for PCT/JP2014/070380; I.A. fd Aug. 1, 2014, dated Mar. 22, 2016, by the International Bureau of WIPO, Geneva, Switzerland.

Servant, G et al., "Positive allosteric modulators of the human sweet taste receptor enhance sweet taste," Proc Natl Acad Sci U S A 2010, Mar. 9;107(10):4746-51. doi: 10.1073/pnas.0911670107. Epub Feb. 19 2010., National Academy of Sciences, Washington, DC.

Galindo-Cuspinera, V et al., "A TAS1R receptor-based explanation of sweet 'water-taste'," Nature. May 18, 2006;441(7091):354-7. Epub Apr. 23, 2006., Nature Publishing Group.

Schiffman, SS et al., "Selective Inhibition of Sweetness by the Sodium Salt of ±2-(4-Methoxyphenoxy)propanoic Acid," Chem Senses. Aug. 1999;24(4):439-47. Oxford University Press, London, England.

Ninomiya, Y, "Reinnervation of cross-regenerated gustatory nerve fibers into amiloride-sensitive and amiloride-insensitive taste receptor cells," Proc Natl Acad Sci U S A. Apr. 28, 1998;95(9):5347-50. National Academy of Sciences, Washington, DC.

Oka, Y, et al., "High salt recruits aversive taste pathways," Nature. Feb. 28, 2013;494(7438):472-5. doi: 10.1038/nature11905. Epub Feb. 13, 2013. Nature Publishing Group.

Bhalla, V et al., "Mechanisms of ENaC regulation and clinical implications," J Am Soc Nephrol. Oct. 2008;19(10):1845-54. doi: 10.1681/ASN.2008020225. Epub Aug. 27, 2008. American Society of Nephrology, Washington, DC.

Yasumoto, K et al., "Isolation of new aliphatic sulfates and sulfamate as the *Daphnia* Kairomones inducing morphological change of a phytoplankton *Scenedesmus gutwinskii*," Chem Pharm Bull (Tokyo). Jan. 2008;56(1):133-6. Pharmaceutical Society of Japan, Tokyo, Japan.

Yasumoto, K et al., "Aliphatic sulfates released from *Daphnia* induce morphological defense of phytoplankton: Isolation and synthesis of kairomones," Tetradedron Letters 46 (2005) 4765-4767, Elsevier, Oxford, England.

(Continued)

*Primary Examiner* — Jeffrey P Mornhinweg
(74) *Attorney, Agent, or Firm* — Sterne, Kessler, Goldstein & Fox P.L.L.C.

(57) ABSTRACT

Provided are a novel compound useful for adjusting sweetness or saltiness or inhibiting ENaC, and use thereof.
An octenyl sulfate ester of the following Formula (1) or a salt thereof, wherein the wavy line represents any one of cis- or trans-configuration.

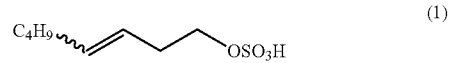

(1)

15 Claims, 1 Drawing Sheet

(56) References Cited

OTHER PUBLICATIONS

La, MP et al., "New bioactive sulfated alkenes from the sea cucumber *Apostichopus japonicas*," Chem Biodivers. Jun. 2012;9(6):1166-71. doi: 10.1002/cbdv.201100324, Verlag Helvetica Chimica Acta, Zürich, Switzerland.

Matsuura, M et al., "Identification and Taste Sensory Evaluation of Naturally Occurring Taste Modifier Octenyl sulfate from Marine Organisms," $58^{th}$ Symposium on the Chemistry of Natural Products, poster session, Sep. 9, 2015, Kanagawa Kenmin Hall, Yokohama City, Nahagawa Prefecture, Japan.

Matsuura, M et al., "Identification of a Sweet Taste Modifier from Hermit Crab," summary of the poster session entitled "Identification and Taste Sensory Evaluation of Naturally Occurring Taste Modifier Octenyl sulfate from Marine Organisms" (attached) orally presented and distributed to the public at the $58^{th}$ Symposium on the Chemistry of Natural Products, Sep. 9, 2015, Kanagawa Kenmin Hall, Yokohama City, Nahagawa Prefecture, Japan.

Terada, I et al., "A novel natural compound acts on human sweet taste receptor," 2014 annual meeting, Japan Society for Bioscience, Biotechnology, and Agrochemistry (JSBBA), Mar. 27-Mar. 30, 2014, Tokyo, Japan, abstract No. 3B07p17 of oral presentation given on Mar. 29, 2014.

\* cited by examiner

ALKENYL SULFATE ESTER OR SALT THEREOF

FIELD OF THE INVENTION

The present invention relates to a novel alkenyl sulfate ester or a salt thereof, and use thereof.

BACKGROUND OF THE INVENTION

In recent years, many low calorie or non-calorie foods and beverages have been marketed for the increase of a disease due to life style such as a metabolic syndrome, or consciousness to health. A substitute sweetener such as a sugar alcohol and an artificial sweetener is mainly used in these products. A sugar alcohol has low sweetness compared to sugar, but is not easily digested and absorbed in the living body. In addition, an artificial sweetener represented by aspartame or Acesulfame K is not easily absorbed in the body or has high sweetness, and thus can impart sufficient sweetness with a low amount. As such, a substitute sweetener can realize a low calorie food or beverage without impairing palatability, and thus is useful.

However, the taste quality of a substitute sweetener is not uniform. In order to impart desired sweetness, a substitute sweetener needs to be used in combination with a different sweetener. For example, aspartame is somewhat slow in rising of sweetness, and has aftertaste of sweetness. Meanwhile, Acesulfame K is early in rising of sweetness and has sharp sweetness. Therefore, combinational use of the two sweeteners presents sweetness closer to natural sugar. In addition, Acesulfame K has a problem of residual aftertaste of bitterness, and is used in combination with another sweetener to suppress the bitterness. In addition, glycyrrhizin, which is a natural product-derived sweetener, is a component that is slow in the rising and strong in aftertaste of sweetness, and the sweetness thereof lasts for a certain time.

A substitute sweetener was originally developed for saving cost. However, these days, a substitute sweetener is considered to be one of means to characterize a product and to add high value to the product to meet various low calorie-oriented consumer needs. Namely, in order to obtain characteristic sweetness that is rich in variety, a substitute sweetener having different taste quality from that of an existing sweetener is desired. Particularly, a long-lasting sweetener is expected for a function such as flavor-reinforcing and flavor-masking. A long-lasting sweetener is highly useful in that it can provide a more delicious food and can reasonably control calorie or sugar intake amount.

A screening for sweeteners using a sweet taste receptor-based assay has been developed since a sweet taste receptor was identified. Guided by the activity against the sweet taste receptor, a component imparting or reinforcing sweetness has been identified (Non Patent Literature 1).

Meanwhile, as a substance imparting sweetness, a component having another activity other than the agonist activity is also conceivable. As one example, lactisole is taken (Non Patent Literature 2). Lactisole has an antagonist activity for a sweet taste receptor, namely, has a sweetness inhibitory effect (Non Patent Literature 2). However, when the lactisole is contained in the mouth, and then water is drunk, the sweetness is induced. The action mechanism thereof is considered to be an inverse agonist activity of lactisole (Non Patent Literature 2). According to the literature, a sweet taste receptor, which is a G protein-coupled receptor, is constitutively active. An inverse agonist such as lactisole decreases the activity below its basal level. When water is drunk in the state where the basic activity is suppressed, the ligand and the receptor are dissociated, and the sweetness receptor returns to the basal state of being weakly activated, and as this time, the sweetness is considered to be induced. In addition, when lactisole is previously contained in the mouth, and a sweetener is taken in the state where the basal activity of the sweetness receptor in the oral cavity is lowered, sweetness reinforcing effect is observed (Non Patent Literature 3). As described above, as a method of inducing sweetness, use of an antagonist such as an inverse agonist is also conceivable.

Sodium chloride is abundant in a normal diet. There is no concern of deficiency in a normal life. However, if a lot of sodium is lost, and the sodium concentration in the blood decreases in the case of a large amount of sweat being bled due to sports, vomit or diarrhea, and heatstroke, it becomes necessary to adequately supply minerals including sodium. For example, it is instructed by Ministry of Health, Labour and Welfare to drink fluid frequently, and take suitable salt in order to prevent heatstroke.

However, if the concentration of mineral components increases in a case where the mineral components are blended with a food and a drink, there are problems that saltiness becomes strong, and the palatability falls. Accordingly, means for inhibiting such saltiness is demanded, and, for example, a method of masking saltiness by adding a saccharide such as inulin (Patent Literature 1) and D-psicose (Patent Literature 2) is known.

In recent years, a voltage-independent sodium channel (hereinafter, also called "ENaC"), of which the activity is inhibited by amiloride, was found as one of the receptors for such saltiness in the oral cavity. It is known that amiloride suppresses only about half of saltiness to the total sense in the oral cavity, inhibiting saltiness in the anterior part of the tongue, but not inhibiting saltiness in the posterior part of the tongue (Non Patent Literature 4). From this, it is considered that amiloride non-sensitive receptors for saltiness are present in addition to ENaC as a receptor for saltiness in the oral cavity, and it is suggested that receptors for bitterness and sour taste are involved as the receptors. Specifically, it is considered that ENaC is involved in a low concentration of 100 mM or less of saltiness, and a receptor for bitterness or sour taste is involved in a high concentration of saltiness (Non Patent Literature 5). Accordingly, it is considered that inhibition of ENaC is effective in inhibition of low concentration of saltiness.

In addition, ENaC is expressed in many human epithelial tissues (for example, the kidney, the bladder, the lungs, the respiratory tract, the salivary gland, and the sweat gland) in addition to the taste bud, and is a route for influx of sodium ion (Non Patent Literature 6). For example, in the kidney, minute control of the sodium amount in the body by means of re-absorption of sodium in the cortical collecting duct is known, which has very important role in regulation of, for example, the body fluid amount, the plasma osmotic pressure, and the blood pressure. Furthermore, it is reported that over-expression or hyperactivity of ENaC is relevant to diseases including hypertension and renal function deterioration, such as cystic fibrosis, pulmonary edema, ulcerative colitis and diarrhea, and ENaC inhibitor is useful for preventing or improving such diseases (see Non Patent Literature 6).

Among known alkenyl sulfate esters, cis/trans-3-decenyl sulfate is reported to be a kairomone-like substance inducing morphological change in green algae (Non Patent Literatures 7 and 8), and trans-3-decenyl sulfate to have an anti-bacterial activity (Non Patent Literature 9). However, an alkenyl sulfate ester adjusting sweetness or saltiness and having ENaC inhibiting action is not known at all until now.

CITATION LIST

Patent Literature

Patent Literature 1: JP 2007-209268 A
Patent Literature 2: JP 5314207 B1

Non Patent Literature

Non Patent Literature 1: Servant, G. et al. Proceedings of the National Academy of Sciences, 2010, 107(10), 4746-4751.
Non Patent Literature 2: Galindo-Cuspinera, V. et al. Nature, 2006, 441, 354-357.
Non Patent Literature 3: Schiffman, S. S. et al. Chemical senses, 1999, 24, 439-447.
Non Patent Literature 4: Ninomiya, Y. Proceedings of the National Academy of Science of the United States of America, 1998, 95, 5347-5350.
Non Patent Literature 5: Oka, Y.; et al. Nature, 494, 472-475 (2013)
Non Patent Literature 6: Bhalla, V.; et al. Journal of American Society of Nephrology. 2008, 19, 1845-1854.
Non Patent Literature 7: Yasumoto, K.; et al. Chemical & Pharmceutical Bulltein, 2008, 56(1), 133-136.
Non Patent Literature 8: Yasumoto, K.; et al. Tetrahedron Letters, 2005, 46, 4765-4767.
Non Patent Literature 9: La, M-P.; et al. CHEMISTRY & BIODIVERSITY, 2012, 9, 1166-1171

SUMMARY OF THE INVENTION

The present invention relates to 1) to 15) described below.
1) An octenyl sulfate ester represented by Formula (1), wherein the wavy line is either cis- or trans-configuration, or a salt thereof.

(1)

2) A sweetness-adjusting agent comprising the octenyl sulfate ester or the salt thereof according to 1) above as an active ingredient.
3) A sweetener composition comprising the octenyl sulfate ester or the salt thereof according to 1) above.
4) A method of imparting or adjusting sweetness with respect to a food or a drug, the method comprising adding the octenyl sulfate ester or the salt thereof according to 1) above or the sweetness-adjusting agent according to 2) above to the food or drug.
5) An epithelial sodium channel inhibitor comprising the octenyl sulfate ester or the salt thereof according to 1) above as an active ingredient.
6) A saltiness inhibitor comprising the octenyl sulfate ester or the salt thereof according to 1) above as an active ingredient.
7) A method of inhibiting saltiness, the method comprising using the saltiness inhibitor of 6) above with respect to a composition containing a salty substance.
8) Use of the octenyl sulfate ester or the salt thereof according to 1) above for manufacturing a sweetness-adjusting agent.
9) Use of the octenyl sulfate ester or the salt thereof according to 1) above for manufacturing a sweetener composition.
10) The octenyl sulfate ester or the salt thereof according to 1) above for use in imparting or adjusting sweetness with respect to a food or a drug.
11) Use of the octenyl sulfate ester or the salt thereof according to 1) above for manufacturing an epithelial sodium channel inhibitor.
12) Use of the octenyl sulfate ester or the salt thereof according to 1) above for manufacturing a saltiness inhibitor.
13) The octenyl sulfate ester or the salt thereof according to 1) above for use in inhibiting an epithelial sodium channel.
14) The octenyl sulfate ester or the salt thereof according to 1) above for use in inhibiting saltiness.
15) A method of inhibiting an epithelial sodium channel, the method comprising administering or taking an effective amount of the octenyl sulfate ester or the salt thereof according to 1) above to a target in need thereof.

DETAILED DESCRIPTION OF THE INVENTION

The present invention relates to providing a novel compound useful for adjusting sweetness or saltiness or inhibiting ENaC, and use thereof.

The present inventors found that an octenyl sulfate ester or a salt thereof is a sweetening agent imparting slow-acting and long-lasting sweetness different from an existing sweetener. The inventors further found that an octenyl sulfate ester or a salt thereof is a sweetness-adjusting agent inhibiting or reinforcing the sweetness of a sweet substance, and has ENaC inhibiting action and saltiness inhibiting action, and can be used as an ENaC inhibitor and a saltiness inhibitor.

The compound of the present invention is useful as a sweetening agent or sweetness-adjusting agent that can exhibit slow-acting and long-lasting sweetness differently from an existing sweetener, and exhibit functions such as flavor-reinforcing and flavor-masking. The compound of the present invention may be used alone, or in combination with another sweetener in, for example, a food and a drug, whereby to impart slow-acting and long-lasting sweetness and provide a more delicious and value-added food.

In addition, the compound of the present invention can be used as an ENaC inhibitor or saltiness inhibitor with respect to, for example, an oral composition and a food containing a salty substance such as sodium chloride, whereby to reduce the saltiness without impairing safety.

As a result, the compound of the present invention can enhance the product value thereof by improving, for example, feeling of use of the oral composition and improving the taste of a food.

In addition, an ENaC inhibitor can be used for preventing or improving diseases developing due to over-expression of ENaC (gain-of-function variation), for example, hypertension, cystic fibrosis, pulmonary edema, ulcerative colitis, and diarrhea.

An octenyl sulfate ester represented by General Formula (1) of the present invention (referred to as the octenyl sulfate ester (1)) is trans-3-octenyl sulfate (1a) or cis-3-octenyl sulfate (1b) represented by the formulae described below, but is preferably the trans form from the point of inhibiting sweetness or saltiness or inhibiting ENaC.

Examples of a suitable salt of the octenyl sulfate ester (1) of the present invention may include pharmaceutically acceptable salts, for example, metal salts such as an alkali metal salt (for example, a sodium salt, and a potassium salt) and an alkaline earth metal salt (for example, a magnesium salt and a calcium salt); nitrogen-containing organic bases such as an ammonium salt, or trimethyl amine, triethyl amine, tributyl amine, pyridine, quinoline, piperidine, imidazole, picoline, dimethylaminopyridine, N,N-dimethyl aniline, N-methyl piperidine, N-methyl morpholine, diethyl amine, cyclohexyl amine, procaine, dibenzyl amine, N-benzyl-β-phenethyl amine, 1-ephenamine, N,N'-dibenzylethylene diamine and N-methyl-β-glucamine; and salts with a basic amino acid such as lysine, arginine and ornithine. Among them, a suitable salt of the octenyl sulfate ester (1) of the present invention is preferably an alkali metal salt, and more preferably a sodium salt or a potassium salt.

In addition, the octenyl sulfate ester (1) of the present invention or a salt thereof can be present not only as a non-solvate, but also as a hydrate or a solvate. Accordingly, in the present invention, the octenyl sulfate ester (1) of the present invention includes all the crystal forms, and hydrates or solvates.

The octenyl sulfate ester (1) of the present invention can be manufactured by, for example, reacting trans-3-octen-1-ol (2) or cis-3-octen-1-ol (3) with a sulfating reagent in an organic solvent whereby to perform sulfuric esterification of trans-3-octen-1-ol (2) or cis-3-octen-1-ol (3).

The sulfating reagent used herein is not particularly limited as long as it can esterify alcohols. Examples of the sulfating reagent include, a sulfur trioxide-pyridine complex, a sulfur trioxide-trimethyl amine complex, a sulfur trioxide-triethyl amine complex, a sulfur trioxide-dimethyl formamide complex, sulfuric acid-dicyclohexyl carbodiimide, chlorosulfuric acid, conc. sulfuric acid, and sulfamic acid. Among them, the sulfating reagent is preferably a sulfur trioxide-pyridine complex.

The reaction solvent is not limited as long as it does not disturb the esterification described above. Examples of a suitable solvent include, tetrahydrofuran, acetonitrile, dimethylformamide, dichloromethane, chloroform, ether, and carbon tetrachloride.

Although the reaction temperature may be set to be from room temperature to around the boiling point of the solvent, it is preferably from −20 to 200° C., and more preferably from 0 to 100° C. In addition, the reaction time is from 0.1 to 48 hours, and preferably from 1 to 12 hours.

The trans-3-octen-1-ol (2), which is used as a starting material, can be obtained by, for example, reacting 1-heptene and paraformaldehyde in the presence of an organic aluminum reagent such as dimethylaluminum chloride (see Snider, B. B; et al. Journal of American Chemical Society, 1982, 104, 555-563.).

In addition, the cis-3-octen-1-ol (3) is generally available, and can be obtained by, for example, subjecting 3-octyn-1-ol to catalytic hydrogenation using a Lindlar catalyst. (see Mayer, S. F.; et al. European Journal of Organic Chemistry, 2001, 4537-4542.)

The salt of the octenyl sulfate ester (1) of the present invention can be obtained from the octenyl sulfate ester (1) at room temperature or by suitably heating the octenyl sulfate ester (1) in the presence of a basic compound such as sodium hydroxide, potassium hydroxide, calcium hydroxide and magnesium hydroxide; a nitrogen-containing organic base such as ammonia, trimethyl amine, triethyl amine, tributyl amine, pyridine, quinoline, piperidine, imidazole, picoline, dimethyl aminopyridine, N,N-dimethyl aniline, N-methyl piperidine, N-methyl morpholine, diethyl amine, cyclohexyl amine, procaine, dibenzyl amine, N-benzyl-β-phenethyl amine, 1-ephenamine, N,N'-dibenzylethylene diamine and N-methyl-D-glucamine; or a basic amino acid such as lysine, arginine and ornithine. In addition, the salt of the octenyl sulfate ester (1) can be obtained by adsorbing the octenyl sulfate ester (1) onto a basic anion exchange resin, and eluting it with an eluent containing the basic compound described above.

Isolation and/or purification of the octenyl sulfate ester (1) of the present invention or a salt thereof obtained by the reactions described above can be carried out by, for example, filtration, washing, drying, recrystallization, or various chromatographies.

Thus-obtained octenyl sulfate ester (1) exhibits slow-acting and long-lasting sweetness as shown in Test Examples 1-4 described later. In addition, the sweetness is promoted by water. Furthermore, the octenyl sulfate ester (1) has an action to adjust the sweetness of another sweetener as shown in Test Examples 5 and 6 described later. Accordingly, the octenyl sulfate ester (1) or a salt thereof can be a sweetening agent that can impart slow-acting and long-lasting sweetness, and can be a sweetness-adjusting agent adjusting the sweetness of another sweetener. Thus, a composition containing the octenyl sulfate ester (1) or a salt thereof can be a sweetener composition. By blending the octenyl sulfate ester (1) or a salt thereof in for example, a food, a drug, and a feed alone or in a form of a composition, it is possible to impart slow-acting and long-lasting sweetness, and adjust the sweetness of coexisting other sweetener (for example, sucrose, aspartame, sucralose, and glycyrrhizin).

Here, the "slow-acting" means that sweetness is not felt immediately at the time of ingestion, but sweetness is felt slowly, and is a synonym for the "aftertaste of sweetness" described below.

The "sweetness-adjusting" means inhibition or reinforcement of the sweetness of another sweet substance other than the octenyl sulfate ester (1) or a salt thereof. Examples of the inhibition of the sweetness preferably include inhibition of the first taste of sweetness immediately after intake of another sweetener. Examples of the reinforcement of sweetness preferably include reinforcement of aftertaste of sweetness remaining in the mouth.

Examples of a specific method for preparing the sweetness of another sweetener using the octenyl sulfate ester (1) or a salt thereof include, a method in which the octenyl sulfate ester (1) or a salt thereof is taken simultaneously with another sweetener whereby to inhibit the first taste of sweetness of another sweetener and further reinforce aftertaste of sweetness of the sweetener remaining in the mouth, or a method in which the octenyl sulfate ester (1) or a salt thereof is taken previously and then another sweetener is taken to reinforce the sweetness of the sweetener. It is assumed that in a case where the octenyl sulfate ester (1) or a salt thereof is taken advance, it reinforces sensitivity of the sweetness of another sweetener.

The sweetener composition of the present invention can be prepared by blending the octenyl sulfate ester (1) or a salt thereof with other additives other than a sweet component such as an excipient, a binder, a disintegrator and a lubricant. The sweetener composition may be in any form such as a powder, a granule, a syrup or a tablet.

In addition, the sweetener composition may contain another sweetener such as a saccharide (for example, sucrose, invert sugar, isomerized sugar, glucose, fructose, lactose, maltose, trehalose, and xylose), a sugar alcohol (for example, maltitol, sorbitol, mannitol, erythritol, xylitol, and lactitol), an oligosaccharide, a dietary fiber, aspartame, saccharin, Acesulfame K, sucralose, thaumatin, stevioside and glycyrrhizin. In this case, while adjusting the sweetness of another sweetener, the sweetener composition can make slow rising of sweetness, and exhibit long-lasting sweetness.

The octenyl sulfate ester (1) of the present invention or a salt thereof, or a sweetener composition including the same can be widely used for imparting or adjusting sweetness with respect to various products requiring sweetness or sweetness-adjusting (subject product for imparting or adjusting sweetness) such as a food, a drug and a feed. Examples of the food include a beverage, and chocolate. In addition, examples of the drug include a powder, a tablet, a solution, and a syrup, and in addition, a dentifrice and a mouthwash, which are treated as a quasi-drug. Examples of the drug also include a drug for an animal having a liking for sweetness.

The sweetener composition of the present invention may be used arbitrarily to a degree necessary in taste for a subject product for imparting or adjusting sweetness. The use amount thereof varies depending on the form of a subject preparation. The sweetener composition of the present invention can be used usually in a concentration of 1/1000 folds or more, preferably a concentration of 1/500 folds or more, and further preferably a concentration of 1/400 folds or more, and a concentration of 1/20 folds or less, preferably a concentration of 1/50 folds or less, further preferably a concentration of 1/100 folds or less, and can be used in a concentration of from 1/1000 folds to 1/20 folds, preferably in a concentration of from 1/500 folds to 1/50 folds, and further preferably in a concentration of from 1/400 folds to 1/100 folds, relatively to the sucrose concentration equal to the required sweetness in a liquid food as the octenyl sulfate ester (1) of the present invention or a salt thereof. In a solid food, the sweetener composition of the present invention can be used in a concentration of 1/1000 folds or more, preferably a concentration of 1/500 folds or more and further preferably a concentration of 1/400 folds or more, and in a concentration of 1/20 folds or less, preferably a concentration of 1/50 folds or less and further preferably a concentration of 1/100 folds or less, and can be used in a concentration of from 1/1000 folds to 1/20 folds, preferably in a concentration of from 1/500 folds to 1/50 folds, and further preferably in a concentration of from 1/400 folds to 1/100 folds, relatively to the sucrose weight equal to the required sweetness.

Examples of a method of using the octenyl sulfate ester (1) or a salt thereof, or a sweetener composition of the present invention in a subject product for imparting or adjusting sweetness include, for example, a method of adding the octenyl sulfate ester (1) or a salt thereof, or a sweetener composition of the present invention to the subject product by adopting a suitable method such as mixing, kneading, dissolution, dipping, penetration, dispersing, spraying and infusion at the time of production of a food or a drug, or at the time of intake or administration of them.

In addition, the octenyl sulfate ester (1) of the present invention inhibits influx of sodium ion into a cell from ENaC, and effectively inhibits saltiness from sodium chloride as shown in Examples described later.

Accordingly, the octenyl sulfate ester (1) or a salt thereof can be an ENaC inhibitor or a saltiness inhibitor, and the octenyl sulfate ester (1) or a salt thereof can be used for manufacturing an ENaC inhibitor or a saltiness inhibitor.

In the present invention, the "ENaC inhibition" means inhibition of influx of sodium ion into a cell from the epithelial sodium channel. Meanwhile, the activity of ENaC inhibition can be tested by measuring inhibitory effect for ENaC in a suitable cell-based assay. For example, single cells or confluent epithelium, endogenously express or to engineered over-express ENaC, can be used to evaluate the channel function using electrophysiological technology (The journal of biological chemistry, 284(2): pages 792-798 (2009)).

ENaC is expressed in the taste bud, and functions as an amiloride-sensitive receptor for saltiness. ENaC is also expressed in many human epithelial tissues such as the kidney, the bladder, the lungs, the respiratory tract, the salivary gland and the sweat gland (Non Patent Literature 6 described above), and manages regulation of the body fluid amount, the plasma penetration pressure, and the blood pressure, and over-expression of ENaC (gain-of-function variation) is known to cause a disease such as hypertension, cystic fibrosis, pulmonary edema, ulcerative colitis and diarrhea (Non Patent Literature 6 described above).

Accordingly, the octenyl sulfate ester (1) or a salt thereof is aimed to prevent or improve the disease described above, and can be used for inhibiting ENaC. Here, the "use" may be used in human or non-human animal, or a sample derived from them, and may be therapeutic use or non-therapeutic use. In addition, the "non-therapeutic" is a concept not including a medical activity, namely, a concept not including surgery, treatment or diagnosis for human, and more specifically a concept not including surgery, treatment or diagnosis for human implemented by a physician or a person instructed by a physician.

Namely, a composition containing the ENaC inhibitor of the present invention is a drug, a quasi-drug or a food exerting effects of inhibiting ENaC, or preventing or improving each disease described above, and the ENaC inhibitor is useful as a material or preparation for being blended with a drug, a quasi-drug or a food. Meanwhile, the food encompasses a food, a functional food, a food for a patient, a specific health food and supplement showing ENaC inhibition or improvement for symptoms of the diseases described above.

The formulation of the drug, quasi-drug or a food is not particularly limited, and each can be prepared by suitably combining acceptable carriers and the octenyl sulfate ester (1) or a salt thereof.

In addition, inhibition of saltiness using the ENaC inhibitor or saltiness inhibitor of the present invention can inhibit the saltiness by using them with respect to a composition containing a salty substance (source substance of saltiness).

Here, the "inhibition of saltiness" encompasses reduction of saltiness, and inhibition of saltiness.

Examples of a composition containing a salty substance include, an oral composition and a food.

Examples of the salty substance include metal ions derived from a mineral such as sodium, potassium, calcium, magnesium and phosphorus, chloride ion, and one, or two or more kinds of metal chloride consisting of the metal ion and chloride ion. Representative examples of the salty substance include sodium chloride and potassium chloride.

Examples of the use mode of the ENaC inhibitor or saltiness inhibitor of the present invention when the ENaC inhibitor or saltiness inhibitor of the present invention is used for inhibiting saltiness mainly include blending of the ENaC inhibitor or saltiness inhibitor with a composition containing a salty substance, and use of the ENaC inhibitor or saltiness inhibitor in combination with a composition containing a salty substance.

Examples of the use of the ENaC inhibitor or saltiness inhibitor in combination with a composition containing a salty substance include, a method in which an aqueous solution of the ENaC inhibitor or saltiness inhibitor is prepared, and this is previously contained in the oral cavity, and then a composition containing a salty substance is taken orally or by another route, or a method in which an aqueous solution of the ENaC inhibitor or saltiness inhibitor and a composition containing a salty substance are taken at the same time orally or by another route.

The ENaC inhibitor or saltiness inhibitor of the present invention may include the octenyl sulfate ester (1) or a salt thereof described above only, or may be blended with one or more raw materials and/or materials usually used in a drug or a food such as water, starch, protein, fiber, sugar, lipid, fatty acid, vitamin, mineral, a flavoring agent, a colorant, a sweetener, a seasoning, an antiseptic, a preservative and an antioxidant. In addition, the form of the ENaC inhibitor or saltiness inhibitor of the present invention may be arbitrary, and may be any form such as a solution form, a suspension form, a syrup form, a powder form, a granule form and a particle form, and may be molded to a desired form.

The form of the composition containing a salty substance (for example, an oral composition, and a food) described above may be a liquid form or paste form such as an aqueous solution, a suspension and an emulsion, or a solid form such as a powder form, a granule form and a particle form. The food may be of any kind such as a general food and a drink, a nutritious food or a functional food, for example, a refreshing beverage, a tea-based beverage, a coffee beverage, a fruit juice beverage, a carbonated beverage, a sports drink, juice, a jelly, a wafer, a biscuit, bread, a noodle and a sausage. Examples of the oral composition include, a dentifrice, a mouthwash, and a gingiva massage cream. Examples of a suitable composition containing a salty substance include various solid foods, beverages, dentifrices, and mouthwashes containing a salty substance.

In a case where the form of the composition is a liquid form or paste form such as an aqueous solution, a suspension and an emulsion in application of the ENaC inhibitor or saltiness inhibitor of the present invention to such composition, a method may be applied in which the ENaC inhibitor or saltiness inhibitor of the present invention is added and sufficiently stirred and dispersed. In addition, in a case where the form of the composition is a solid form such as a powder, a method may be applied in which the ENaC inhibitor or saltiness inhibitor of the present invention is simply added and mixed.

In a case where the ENaC inhibitor or saltiness inhibitor of the present invention is used with respect to a composition containing a salty substance, the ENaC inhibitor or saltiness inhibitor is preferably used such that the octenyl sulfate ester (1) of the present invention or a salt thereof is used in 0.001 parts by mass or more, preferably 0.01 parts by mass or more, and 90 parts by mass or less, preferably 10 parts by mass or less relatively to one part by mass of the salty substance. In addition, the ENaC inhibitor or saltiness inhibitor is used in from 0.001 to 90 parts by mass, and preferably from 0.01 to 10 parts by mass.

The content of the octenyl sulfate ester (1) or a salt thereof in a drug, a quasi-drug or a food containing the octenyl sulfate ester (1) of the present invention or a salt thereof is not particularly limited, and is 0.1% by mass or more, preferably 1% by mass or more and further preferably 10% by mass or more, and 99% by mass or less, preferably 90% by mass or less and further preferably 50% by mass or less relatively to the total mass of the preparation. In addition, the content of the octenyl sulfate ester (1) or a salt thereof is, for example, from 0.1 to 99% by mass, preferably from 1 to 90% by mass and further preferably from 10 to 50% by mass.

The dose of the octenyl sulfate ester (1) of the present invention or a salt thereof in a case where the octenyl sulfate ester (1) of the present invention or a salt thereof is blended with a drug or supplement and is used, may vary depending on conditions, body weight, sex and age of a target person or other factors. The dose per day for an adult in the case of oral administration is usually 0.1 mg or more, preferably 1 mg or more and further preferably 5 mg or more, and 10 g or less, preferably 1 g or less and further preferably 500 mg or less as the octenyl sulfate ester (1) or a salt thereof. In addition, the dose is, for example, from 0.1 mg to 10 g, preferably from 1 mg to 1 g and further preferably from 5 mg to 500 mg.

The preparation described above may be administered according to arbitrary administration regimen but is preferably administered once to several times per day in division continuously for weeks to months. In addition, examples of the target for administration or intake include human in need or desire thereof, for example, human in need or desire to prevent or improve diseases due to ENaC over-expression such as hypertension and a renal function disorder.

Regarding to the embodiments described above, the modes described below are disclosed in the present invention.

<1> An octenyl sulfate ester of Formula (1), wherein the wavy line is either cis- or trans-configuration, or a salt thereof.

(1)

<2> A sweetness-adjusting agent comprising the octenyl sulfate ester or the salt thereof according to <1> above as an active ingredient.

<3> The sweetness-adjusting agent according to <2> above, inhibiting the first taste of sweetness of another sweetener.

<4> The sweetness-adjusting agent according to <3> above, further reinforcing the aftertaste of sweetness of the other sweetener.

<5> The sweetness-adjusting agent according to <2> above, which reinforces the sweetness of another sweetener in a case where an octenyl sulfate ester or a salt thereof is previously taken, and then the other sweetener is taken.

<6> In <3> to <5> above, examples of the other sweeteners include sucrose, aspartame, sucralose and glycyrrhizin and glycyrrhizin is preferable.

<7> A sweetener composition comprising the octenyl sulfate ester or the salt thereof according to <1> above.

<8> A method of imparting or adjusting sweetness with respect to a food or a drug, the method comprising adding the octenyl sulfate ester or the salt thereof according to <1> above or the sweetness-adjusting agent according to any one of <2> to <5> above to the food or drug.

<9> Use of the octenyl sulfate ester or the salt thereof according to <1> above for manufacturing a sweetness-adjusting agent.

<10> Use of the octenyl sulfate ester or the salt thereof according to <1> above for manufacturing a sweetener composition.

<11> In the sweetener composition of <7> or <10>, the sweetness is slow-acting sweetness.

<12> The octenyl sulfate ester or the salt thereof according to <1> above for use in imparting or adjusting sweetness with respect to a food or a drug.

<13> An epithelial sodium channel inhibitor comprising the octenyl sulfate ester or the salt thereof according to <1> above as an active ingredient.

<14> A saltiness inhibitor comprising the octenyl sulfate ester or the salt thereof according to <1> above as an active ingredient.

<15> Use of the octenyl sulfate ester or the salt thereof according to <1> above for manufacturing an epithelial sodium channel inhibitor.

<16> Use of the octenyl sulfate ester or the salt thereof according to <1> above for manufacturing a saltiness inhibitor.

<17> The octenyl sulfate ester or the salt thereof according to <1> above for use in inhibiting an epithelial sodium channel.

<18> The octenyl sulfate ester or the salt thereof according to <1> above for use in inhibiting saltiness.

<19> A method of inhibiting an epithelial sodium channel, the method comprising administering or taking an effective amount of the octenyl sulfate ester or the salt thereof according to <1> above to a target in need thereof.

<20> A method of inhibiting the saltiness of a composition containing a salty substance, the method comprising using the epithelial sodium channel inhibitor according to <13> or the saltiness inhibitor according to <14> with respect to the composition containing a salty substance.

<21> The method according to <20>, wherein the epithelial sodium channel inhibitor or saltiness inhibitor is blended with a composition containing a salty substance and is used.

<22> The method according to <20> or <21>, wherein the composition containing a salty substance is a composition containing mineral-derived metal ion and/or chloride ion, or metal chloride consisting of the metal ion and chloride ion.

<23> The method according to <22>, wherein the mineral is one or more kinds of metal selected from the group consisting of sodium, potassium, calcium, magnesium and phosphorus.

<24> The method according to any one of <20> to <23>, wherein the composition is a food or an oral composition.

<25> The method of any one of <20> to <24>, wherein the octenyl sulfate ester (1) or a salt thereof is used in 0.001 parts by mass or more, preferably 0.01 parts by mass or more, and 90 parts by mass or less, preferably 10 parts by mass or less, or used in from 0.001 to 90 parts by mass, preferably from 0.01 to 10 parts by mass relatively to one part by mass of the salty substance.

EXAMPLES

Preparation Example 1 Synthesis of Cis-3-Octenyl Sulfate

To cis-3-octen-1-ol (manufactured by Tokyo Chemical Industry Co., Ltd., 256 mg, 2.00 mmol), tetrahydrofuran (20 mL) and sulfur trioxide pyridine (600 mg, 2 mmol) were added and the reaction mixture was stirred overnight. Subsequently, the reaction mixture was basified with 1M aqueous solution of NaOH, and then dry nitrogen was sprayed and tetrahydrofuran was removed. The residue was loaded onto a ODS column (COSMOSIL 140C18 OPN, 10 g, manufactured by Nacalai Tesque), and then washed with water, and eluted with 20% aqueous acetonitrile, and the obtained eluting solution was concentrated and dried under reduced pressure, whereby to obtain cis-3-octenyl sulfate (81 mg).

Characteristics: white powder, 185° C. melting point (decomposition);

$^1$H NMR (600 MHz, CD$_3$OD): δ 0.92 (3H, t, J=7.8 Hz, H-8), 1.33-1.37 (4H, m, H-6, 7), 2.08 (2H, m, H-5), 2.42 (2H, tddd, J=7.2, 7.2, 1.0, 1.0 Hz, H-2), 3.96 (2H, t, J=7.2 Hz, H-1), 5.40 (1H, dtt, J=10.7, 7.2, 1.2 Hz, H-3), 5.49 (1H, dtt, J=10.7, 7.7, 1.0 Hz, H-4)

$^{13}$C NMR (150 MHz, CD$_3$OD): δ 14.33 (C-8), 23.25 (C-7), 27.99 (C-6), 28.55 (C-5), 32.98 (C-2), 68.57 (C-8), 125.69 (C-3), 133.46 (C-4)

Preparation Example 2 Synthesis of Trans-3-Octenyl Sulfate

To 1-heptene (196 mg, 2 mmol), methylene chloride (6 mL) and paraformaldehyde (60 mg, 2 mmol) were added, and then the reaction mixture was cooled to 0° C., dropped with 1.08M dimethylaluminum chloride-hexane solution (2.77 mL, 3 mmol), warmed up to room temperature and then stirred overnight. Subsequently, the reaction mixture was added with a saturated aqueous solution of sodium dihydrogen-phosphate (2 mL) and 1M aqueous solution of hydrochloride (3 mL), and then extracted with ether (10 mL) three times repeatedly. The obtained ether layer was dried with sodium sulfate, and then concentrated under reduced pressure, whereby to obtain trans-3-octen-1-ol (190 mg, 1.48 mmol). Subsequently, the obtained trans-3-octen-1-ol (190 mg, 1.48 mmol) was added with tetrahydrofuran (15 mL) and sulfur trioxide pyridine (421 mg, 1.63 mmol) and stirred overnight. Subsequently, the reaction mixture was basified with 1M aqueous solution of NaOH, and then dry nitrogen was sprayed and tetrahydrofuran was removed. The residue was loaded onto a ODS column (COSMOSIL 140C18 OPN, 10 g, manufactured by Nacalai Tesque), and then washed with water, and eluted with 20% aqueous acetonitrile. The obtained eluting solution was concentrated and dried under reduced pressure, whereby to obtain trans-3-octenyl sulfate (115 mg).

Characteristics: white powder, 159° C. melting point (decomposition);

1H NMR (600 MHz, $CD_3OD$): δ 0.90 (3H, t, J=7.5 Hz, H-8), 1.29-1.38 (4H, m, H-6, 7), 2.01 (2H, dtt, J=6.8, 6.8, 1.2 Hz, H-5), 2.35 (2H, dtd, J=6.8, 6.8, 1.2 Hz, H-2), 3.97 (2H, t, J=6.8 Hz, H-1), 5.44 (1H, dtt, J=15.3, 6.8, 1.2 Hz, H-3), 5.55 (1H, dtt, J=15.3, 6.8, 1.2 Hz, H-4)

$^{13}C$ NMR (150 MHz, $CD_3OD$): δ 14.28 (C-8), 23.23 (C-7), 32.78 (C-6), 30.40 (C-5), 33.72 (C-2), 68.89 (C-8), 126.62 (C-3), 134.22 (C-4)

Test Example 1 Evaluation of Sweetness (1)

Trans-3-octenyl sulfate was dissolved in water to be 1 wt %, which was taken as a test sample. Six examiners kept 50 μL of the prepared test sample in their mouth, and then drunk some water, and judged for presence or absence of sweetness. As a result, as shown in Table 1, six out of the six examiners recognized the sweetness, and the sweetness lasted for a certain time.

TABLE 1

| | Sweetness felt | No sweetness felt |
|---|---|---|
| 1% Trans-3-octenyl sulfate (50 μL) + Water (13 ml) | 6 | 0 |

Test Example 2 Evaluation of Sweetness (2)

Cis-3-octenyl sulfate was dissolved in water to 1 wt %, which was taken as a test sample. Four examiners kept 50 μL of the prepared test sample in their mouth, and then drunk some water, and judged presence or absence of sweetness. As a result, as shown in Table 2, four out of the four examiners recognized the sweetness, and the sweetness lasted for a certain time.

TABLE 2

| | Sweetness felt | No sweetness felt |
|---|---|---|
| 1% Cis-3-octenyl sulfate (50 μL) + Water (13 ml) | 4 | 0 |

Test Example 3 Evaluation of Sweetness (3)

To seven examiners, 4 kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL solution of 10 mM trans-3-octenyl sulfate in their mouth for 5 seconds or so, and then spat the solution out, and compared the sweetness intensity at that time with that of the aqueous sucrose standard solution, and evaluated the sweetness intensity with a number in a range of 0 to 15. Then, the examiners kept 10 mL pure water for 5 minutes at an interval of 30 seconds, and then spat the solution out, and evaluated the sweetness intensity at that time in the same manner. As a result, as shown in Table 3, Seven out of the seven examiners recognized the sweetness by virtue of intake of water, and the sweetness lasted for a certain time.

TABLE 3

| Time (minute) | Sweetness intensity (mean) | Standard error |
|---|---|---|
| 0 | 0.0 | 0.0 |
| 0.5 | 1.7 | 0.5 |
| 1 | 3.6 | 0.7 |
| 1.5 | 3.9 | 0.8 |
| 2 | 3.6 | 0.5 |
| 2.5 | 3.0 | 0.5 |
| 3 | 2.1 | 0.7 |
| 3.5 | 1.1 | 0.5 |
| 4 | 0.8 | 0.3 |
| 4.5 | 0.5 | 0.3 |
| 5 | 0.6 | 0.4 |

Test Example 4 Evaluation of Sweetness (4)

To seven examiners, four kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL solution of 10 mM cis-3-octenyl sulfate in their mouth for 5 seconds or so, and then spat the solution out, and compared the sweetness intensity at that time with that of the aqueous sucrose standard solution, and evaluated the sweetness intensity with a number in a range of 0 to 15. Then, the examiners kept 10 mL pure water in their mouth for 5 minutes at an interval of 30 seconds, and then spat the solution out, and evaluated the sweetness intensity at that time in the same manner. As a result, as shown in Table 4, seven out of the seven examiners recognized the sweetness by virtue of intake of water, and the sweetness lasted for a certain time.

TABLE 4

| Time (minute) | Sweetness intensity (mean) | Standard error |
|---|---|---|
| 0 | 0.0 | 0.0 |
| 0.5 | 1.8 | 0.6 |
| 1 | 3.2 | 0.4 |
| 1.5 | 3.4 | 0.4 |
| 2 | 2.6 | 0.5 |
| 2.5 | 2.1 | 0.5 |
| 3 | 1.4 | 0.5 |
| 3.5 | 1.4 | 0.5 |
| 4 | 0.9 | 0.3 |
| 4.5 | 0.5 | 0.3 |
| 5 | 0.5 | 0.3 |

Test Example 5 Sweetness Adjusting Action (1) Action on Sucrose

To seven examiners, four kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL aqueous solution (7.5 wt %) of sucrose in their mouth for 5 seconds or so without knowing the kind and the concentration of the sweetener, and then spat the solution out, and compared the sweetness intensity at that time with that of the aqueous sucrose standard solution, and evaluated the sweetness intensity with a number in a range of 0 to 15. In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. Subsequently, the examiners were presented with 10 mL aqueous sucrose solution containing 5 mM trans-3-octenyl sulfate (7.5 wt %), and kept it in their mouth for 5 seconds or so, and then spat the solution out, and compared the sweetness intensity at that time with the sweetness intensity of the aqueous sucrose standard solution, and evaluated the sweetness intensity in the same manner. In addition, immediately after that, the examiners kept 10 mL pure water in their mouth for 5 seconds or so, and then spat the solution out, and compared the sweetness intensity at that time with that of the aqueous sucrose standard solution, and evaluated the sweetness intensity in the same manner. In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. The results are shown in Table 5 described below.

(2) Action on Aspartame

To seven examiners, 4 kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL aqueous solution of aspartame (494 ppm) in their mouth for 5 seconds or so without knowing the kind and the concentration of the sweetener, and then spat the solution out, and compared the sweetness intensity at that time with that of the aqueous sucrose standard solution, and evaluated the sweetness intensity with a number in a range of 0 to 15. The concentration of aspartame was prepared to have the same sweetness intensity as that of the aqueous sucrose solution (7.5 wt %) in accordance with the reference (Schiffman, S. S. et al. Chemical senses, 1999, 24, 439-447.). In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. Subsequently, the examiners were presented with 10 mL aqueous solution of aspartame containing 5 mM trans-3-octenyl sulfate (494 ppm), and kept it in their mouth for 5 seconds or so, and then spat the solution out, and compared the sweetness intensity at that time with the sweetness intensity of the sucrose standard solution, and evaluated the sweetness intensity in the same manner. In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. The results are shown in Table 5.

(3) Action on Sucralose

Six examiners evaluated the sweetness intensity in the same manner as (2) changing 10 mL aqueous solution of aspartame (494 ppm) to 10 mL aqueous solution of sucralose (0.49 mM). The results are shown in Table 5.

(4) Action on Glycyrrhizin

To six examiners, 4 kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL aqueous solution of glycyrrhizin (303 ppm) in their mouth for 5 seconds or so without knowing the kind and the concentration of the sweetener, and then spat the solution out, and compared the sweetness intensity at that time with that of the aqueous sucrose standard solution, and evaluated the sweetness intensity with a number in a range of 0 to 15. The concentration of glycyrrhizin was prepared to have the same sweetness intensity as that of the aqueous solution of sucrose (5 wt %) in accordance with the reference (Schiffman, S. S. et al. Chemical senses, 1999, 24, 439-447.). In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. Subsequently, the examiners were presented with 10 mL aqueous solution of glycyrrhizin containing 5 mM trans-3-octenyl sulfate (494 ppm), and kept it in their mouth for 5 seconds or so, and then spat the solution out, and compared the sweetness intensity at that time with the sweetness intensity of the sucrose standard solution, and evaluated the sweetness intensity in the same manner. In addition, after 30 seconds, the examiners kept 10 mL pure water in their mouth, and then spat the solution out, and compared the sweetness intensity felt at that time with that of the aqueous sucrose standard solution, and evaluated the sweetness intensity in the same manner. The results are shown in Table 5.

TABLE 5

| Sample | Sweetness intensity (mean) | |
|---|---|---|
| | When drinking sample | When drinking water after 30 seconds |
| Sucrose | 7.1 | 0.1 |
| Sucrose + Trans-3-octenyl sulfate | 1.4 | 3.1 |
| Aspartame | 7.1 | 1.0 |
| Aspartame + Trans-3-octenyl sulfate | 1.3 | 2.3 |
| Sucralose | 8.4 | 0.4 |
| Sucralose + Trans-3-octenyl sulfate | 0.7 | 2.3 |
| Glycyrrhizin | 4.1 | 3.2 |
| Glycyrrhizin + Trans-3-octenyl sulfate | 0.2 | 7.9 |

From Table 5, it was found that trans-3-octenyl sulfate inhibits the first taste of sweetness immediately after taking sucrose, aspartame, sucralose or glycyrrhizin, and reinforces the aftertaste of sweetness remaining in the mouth. Particularly, in the case of glycyrrhizin, which has strong aftertaste of sweetness and is a long-lasting sweetener, the reinforcement effect was remarkable.

Test Example 6 Action of Reinforcing Sweetness (1) Sucralose

To six examiners, 4 kinds of 10 mL aqueous solutions of sucrose standard (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL aqueous solution of sucralose (0.25 mM) in their mouth for 5 seconds or so without knowing the kind and the concentration of the sweetener, and then spat the solution out, and compared the sweetness intensity at that time with that of the aqueous sucrose standard solution, and evaluated the sweetness intensity with a number in a range of 0 to 15. Subsequently, the examiners kept 10 mL solution of 5 mM trans-3-octenyl sulfate in advance in their mouth for 5 seconds or so in advance, and then spat the solution out, and after passage of 60 seconds, the examiners kept 10 mL aqueous solution of sucralose (0.25 mM) in their mouth for 5 seconds or so, and then spat the solution out, and compared the sweetness intensity at that time with that of the aqueous sucrose standard solution, and evaluated the sweetness intensity with a number in a range of 0 to 15.

(2) Glycyrrhizin

To six examiners, 4 kinds of 10 mL aqueous sucrose standard solutions (2.5, 5.0, 7.5 and 10.0 wt %) were presented. The examiners kept each of the solutions in their mouth for 5 seconds or so, and then spat the solution out, and were asked to consider the sweetness intensity at that time (0 to 15) to be 2.5, 5, 7.5 and 10, respectively. Next, the examiners kept 10 mL aqueous solution of glycyrrhizin (0.25 mM) in their mouth for 5 seconds or so without knowing the kind and the concentration of the sweetener, and then spat the solution out, and compared the sweetness intensity at that time with that of the aqueous sucrose standard solution, and evaluated the sweetness intensity with a number in a range of 0 to 15. Subsequently, the examiners kept 10 mL solution of 5 mM trans-3-octenyl sulfate in their mouth for 5 seconds or so in advance, and then spat the solution out, and after passage of 60 seconds, the examiners kept 10 mL aqueous solution of glycyrrhizin (0.25 mM) in their mouth for 5 seconds or so, and then spat the solution out, and compared the sweetness intensity at that time with that of the aqueous sucrose standard solution, and evaluated the sweetness intensity with a number in a range of 0 to 15. The results are shown in Table 6.

TABLE 6

| Sample | Trans-3-octenyl sulfate | Sweetness intensity (mean) |
|---|---|---|
| Sucralose (0.25 mM) | No previous intake | 7.3 |
| Sucralose (0.25 mM | Previous intake | 10.2 |
| Glycyrrhizin (0.25 mM) | No previous intake | 3.4 |
| Glycyrrhizin (0.25 mM) | Previous intake | 7.3 |

From Table 6, it was found that with previous intake of trans-3-octenyl sulfate, it has an effect of reinforcing the sweetness of the sweetener.

Test Example 7 ENaC Inhibition Activity of Octenyl Sulfate Ester

Inhibition activity of ENaC expressed in *Xenopus* oocytes was measured according to the method described in "The journal of biological chemistry, 284 (2): pages 792-798 (2009)". Specifically, trans-3-octenyl sulfate was added to oocytes expressed with ENaC complex, and the activity of ENaC was analyzed electrophysiologically in accordance with the procedures described below.

First, DNA sequences encoding human ENaCα, β and γ, respectively were obtained by carrying out PCR using a plasmid vector on which the same gene was cloned (manufactured by Clontech Laboratories, Inc.) as a template. The obtained PCR amplification fragment was integrated into a transcription vector pSP64 (manufactured by Promega Corporation), and pSP64/ENaCα, pSP64/ENaCβ and pSP64/ENaCγ were manufactured, respectively.

pSP64/ENaCα and pSP64/ENaCγ were digested with EcoRI, and pSP64/ENaCβ was digested with PvuII, respectively, whereby linearize the plasmid DNA. With respect to these linearized DNAs, SP6RNA polymerase (manufactured by TAKARA BIO INC.) was used whereby to synthesize cRNA added with polyA sequence expressing ENaCα, ENaCβ and ENaCγ, respectively. The synthesized cRNA was treated with phenol and chloroform, and the obtained supernatant was collected, and further mixed with isopropyl alcohols and centrifuged whereby to precipitate cRNA. The precipitated cRNA was washed with 75% ethanol, and then was dissolved in distilled water to be 1 mg/ml of the concentration.

The obtained aqueous solutions of cRNA encoding ENaCα, ENaCβ and ENaCγ respectively were mixed in the same quantity, and injected by 50 ng per one *Xenopus* oocyte. Specifically, the cRNA aqueous solution was filled into a glass capillary using a manipulator (manufactured by NARISHIGE Group.) and injected by 50 nL per one oocyte. Then, ENaC α, β and γ complexes were expressed on the membrane of the oocyte over 2-3 days.

Two micro-glass electrodes were inserted into the oocyte, and the membrane potential was fixed at −60 mV. At this time, $Na^+$ ion influx induced by ENaC complex in a constantly active state was measured with replacement to change of the current amount. Namely, in 115 mM NaCl solution (115 mM NaCl, 2.5 mM KCl, 1.8 mM $CaCl_2$, 1 mM $NaHCO_3$, 1 mM $MgCl_2$ and 10 mM HEPES, pH 7.4) and under circumstances where inward current was caused by the oocytes, trans-3-octenyl sulfate dissolved in the same solution was administered.

Figure 1:
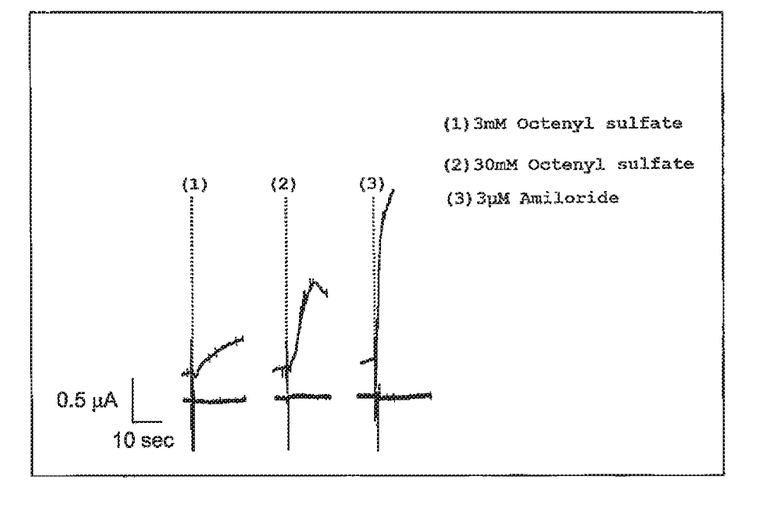
FIG. 1 illustrates ENaC inhibiting effects.

As a result, as shown in FIG. 1, trans-3-octenyl sulfate inhibited inward current of ENaC expressing oocytes concentration-dependently in a range of 3 to 30 mM. This effect was similar to that of an existing ENaC inhibitor amiloride. In addition, this effect of trans-3-octenyl sulfate was not recognized in oocytes not expressing ENaC, and from this, it was confirmed that the effect of trans-3-octenyl sulfate is directed to ENaC.

Test Example 8

7 subjects were presented with 0.6 w/v saline as a saltiness standard solution, and kept it in their mouth for 5 seconds or so, and then spat the solution out. The saltiness intensity felt (0 to 10) was assumed to be 5.

Then, the subjects kept the aqueous saline solution (0.6 and 1.0 w/v %) respectively in their mouth for 5 seconds or so, and then spat the solution out. The intensity felt was responded in a range of 1 to 10 wherein 0 refers to no feeling and 10 refers to very strong feeling. Subsequently, aqueous saline solutions containing 5 mM trans-3-octenyl sulfate (0.6 and 1.0 w/v %) were prepared, and presented to the examiners. The examiners kept the aqueous solutions respectively in their mouth for 5 seconds or so, and then spat the solutions out. The intensity felt was responded in a value of 0 to 10. The results are shown in Table 7.

TABLE 7

|  | Concentration of saline (weight %) | Trans-3-octenyl sulfate | Saltiness intensity (mean) |
|---|---|---|---|
| Sample 1 | 0.6 | — | 5.2 |
| Sample 2 | 0.6 | 5 mM | 3.2 |
| Sample 3 | 1.0 | — | 7.2 |
| Sample 4 | 1.0 | 5 mM | 4.0 |

From Table 7, it was confirmed that the octenyl sulfate ester of the present invention has a saltiness inhibiting action.

The invention claimed is:

1. A composition comprising an octenyl sulfate ester of Formula (1), (1)

wherein the wavy line is either a cis- or trans-configuration, or a salt thereof,
and an additional sweetener other than the octenyl sulfate ester of Formula (1) or salt thereof.

2. The composition of claim 1, wherein the composition is a food, feed, drug or quasi-drug.

3. The composition according to claim 1, wherein the octenyl sulfate ester of Formula (1) or salt thereof inhibits the first taste of sweetness of the other sweetener.

4. The composition according to claim 3, wherein the octenyl sulfate ester of Formula (1) or salt thereof reinforces the sweetness aftertaste of the other sweetener.

5. The composition according to claim 3 or 4, wherein the other sweetener is glycyrrhizin.

6. A method for reinforcing the sweetness of a sweetener, the method comprising
    (a) administering or taking an octenyl sulfate ester of Formula (1), (1)

wherein the wavy line is either a cis- or trans-configuration, or a salt thereof,
followed by
(b) administering or taking a sweetener other than the octenyl sulfate ester of Formula (1) or salt thereof, to or by a target.

7. The method according to claim 6, wherein the aftertaste of the sweetener administered or taken in step (b) is reinforced.

8. A method of imparting sweetness to, or adjusting the sweetness of, a food or a drug, the method comprising adding an octenyl sulfate ester of Formula (1), (1)

wherein the wavy line is either a cis- or trans-configuration,
or a salt thereof to the food or drug.

9. A composition comprising an epithelial sodium channel inhibitor that comprises
    an octenyl sulfate ester of Formula (1), (1)

wherein the wavy line is either a cis- or trans-configuration,
or a salt thereof,
as an active ingredient,
wherein the composition is a dentifrice, a mouthwash or a gingiva massage cream, and
wherein the composition also contains a salty substance.

10. The composition of claim 9, wherein the composition is a mouthwash.

11. A method of inhibiting the saltiness of a composition comprising a salty substance, the method comprising
    (a) administering or taking a saltiness inhibiting amount of an octenyl sulfate ester of Formula (1):

(1)

wherein the wavy line is either cis- or trans-configuration, or a salt thereof and,
(b) administering or taking the composition that comprises the salty substance to or by a target in need of the inhibiting.

12. The method according to claim 11, wherein the composition comprising the salty substance is a composition comprising mineral-derived metal ion and/or chloride ion, or metal chloride consisting of the metal ion and chloride ion.

13. The method according to claim 12, wherein the mineral is at least one metal selected from the group consisting of sodium, potassium, calcium, magnesium and phosphorus.

14. The method according to claim 11, wherein the composition is a food or an oral composition.

15. A method of inhibiting an epithelial sodium channel, the method comprising administering or taking of an effective amount of the octenyl sulfate ester of Formula (1):

(1)

wherein the wavy line is either a cis- or trans-configuration,
or a salt thereof
to or by a target in need thereof.

* * * * *